US009034259B2

(12) United States Patent
Kanda

(10) Patent No.: US 9,034,259 B2
(45) Date of Patent: May 19, 2015

(54) FLOW CYTOMETER AND FLOW CYTOMETRY

(75) Inventor: Masahiko Kanda, Hyogo (JP)

(73) Assignee: BAY BIOSCIENCE KABUSHIKI KAISHA, Hyogo (JP)

(*) Notice: Subject to any disclaimer, the term of this patent is extended or adjusted under 35 U.S.C. 154(b) by 453 days.

(21) Appl. No.: 13/064,837

(22) Filed: Apr. 20, 2011

(65) Prior Publication Data

US 2011/0259749 A1 Oct. 27, 2011

(30) Foreign Application Priority Data

Apr. 23, 2010 (JP) .................................. 2010-099608

(51) Int. Cl.
| | | |
|---|---|---|
| *C12Q 1/68* | (2006.01) | |
| *G01N 15/06* | (2006.01) | |
| *G01N 33/00* | (2006.01) | |
| *G01N 21/00* | (2006.01) | |
| *B01L 3/00* | (2006.01) | |
| *G01N 15/14* | (2006.01) | |

(52) U.S. Cl.
CPC ........ *G01N 15/14* (2013.01); *G01N 2015/1406* (2013.01); *G01N 2015/149* (2013.01)

(58) Field of Classification Search
CPC .................... G01N 15/1459; G01N 2015/149; G01N 2015/1477; G01N 15/1429; G01N 15/1463; G01N 2015/1438; G01N 15/1427; G01N 15/1456; G01N 2015/0065; G01N 2015/1413; G01N 2015/1454; G01N 2015/1472; G01N 2015/1486; G01N 2021/4707; G01N 2021/6471; G01N 21/51; G01N 21/645; G01N 2201/06113; G01N 33/5005; G01N 15/14; G01N 2015/1406
USPC .......... 422/50, 68.1, 73, 82.05, 500, 501, 930
See application file for complete search history.

(56) References Cited

U.S. PATENT DOCUMENTS 5,776,781 A * 7/1998 Vardanega et al. ............. 436/63
6,880,414 B2 4/2005 Norton
(Continued)

FOREIGN PATENT DOCUMENTS

| JP | H08-015125 | 1/1996 |
|---|---|---|
| JP | 2004069706 A | 3/2004 |
| JP | 2005-315799 | 11/2005 |

OTHER PUBLICATIONS

Japanese Office Action and English translation thereof dated Sep. 3, 2013.

*Primary Examiner* — Dean Kwak
(74) *Attorney, Agent, or Firm* — Harness, Dickey & Pierce, P.L.C.

(57) ABSTRACT

One embodiment of the present invention is to provide a system for sorting cell particles in a liquid flow, which comprises a flow-defining block including a flow chamber receiving a sample conduit and a flow cell having a flow channel. The system also comprises a strobe block including a imaging device for taking an image of a jet flow ejected from the flow-defining block and a plurality of droplets in a given image area. The flow-defining block and the strobe block are detachably connected each other. Further the strobe block includes a nozzle plate having a nozzle channel between a receiving end and a nozzle. The flow-defining block includes a discharge end opposite to the receiving end and a channel enlarged portion of which cross section taken along a predetermined plane perpendicular to a flow direction has an area increasing towards the discharge end. The discharge end and the receiving end have substantially the same open distance in the predetermined plane perpendicular to the flow direction.

13 Claims, 6 Drawing Sheets

(56) References Cited

U.S. PATENT DOCUMENTS

| | | | |
|---|---|---|---|
| 7,417,734 B2* | 8/2008 | Kanda | 356/337 |
| 7,443,491 B2 | 10/2008 | Kanda | |
| 2005/0112541 A1* | 5/2005 | Durack et al. | 435/2 |
| 2007/0148043 A1* | 6/2007 | Norton et al. | 422/73 |
| 2009/0122311 A1 | 5/2009 | Kanda | |
| 2010/0297759 A1 | 11/2010 | Kanda | |
| 2011/0134426 A1* | 6/2011 | Kaduchak et al. | 356/337 |

\* cited by examiner

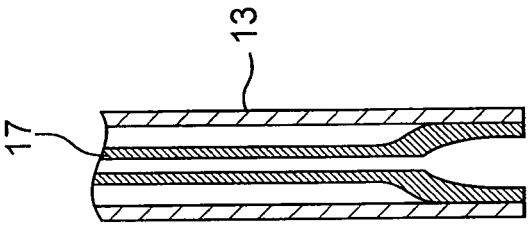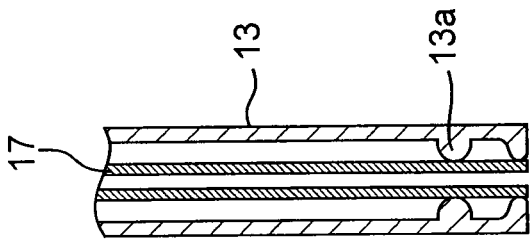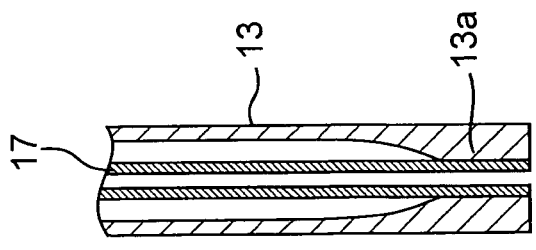

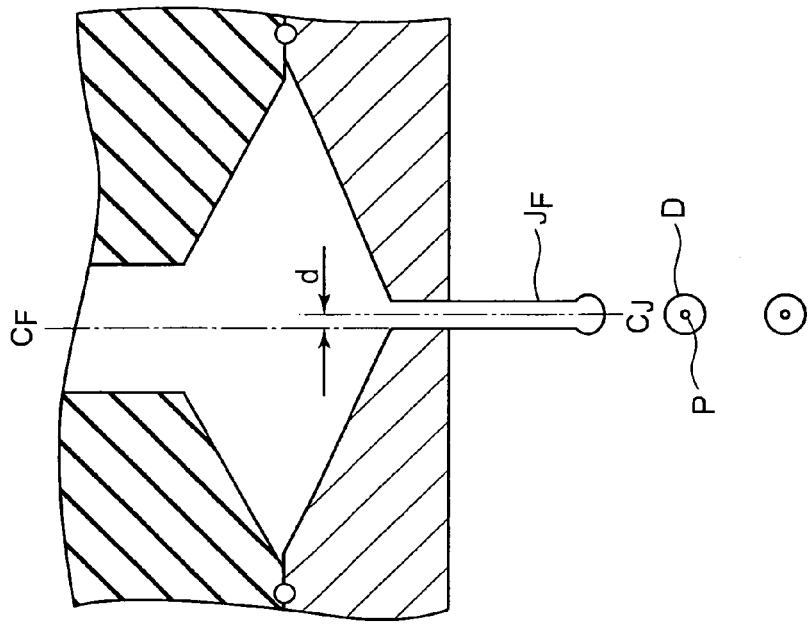
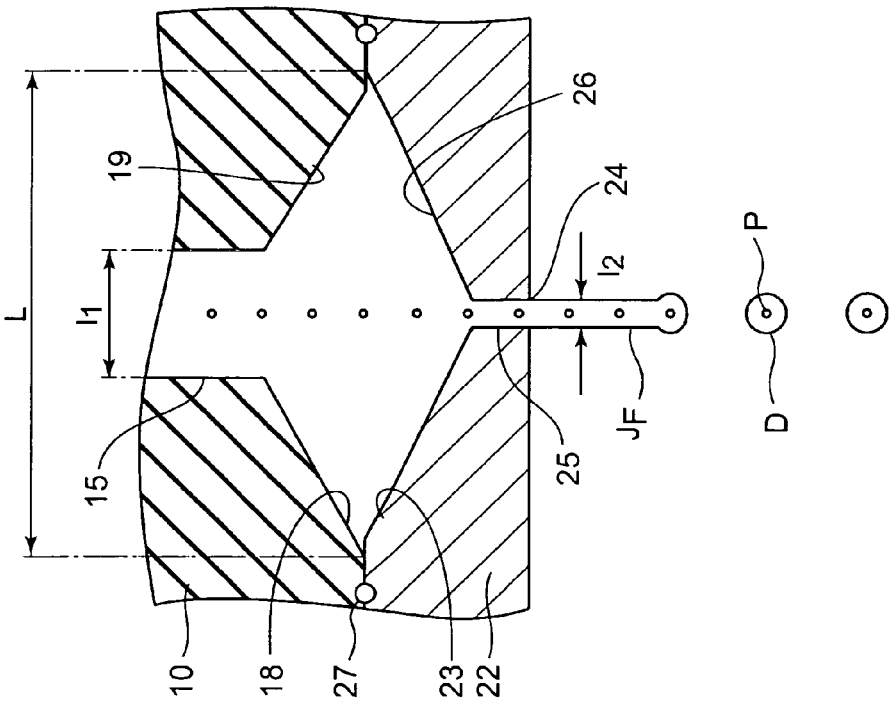

FLOW CYTOMETER AND FLOW CYTOMETRY

TECHNICAL FIELD

The present invention relates to a flow cytometer and a flow cytometry, and in particular to the flow cytometer and the flow cytometry, which allows a series of steps of analyzing and sorting different cell particles within liquid flows, preventing cell particles in the previous liquid flow from being remaining in or contaminating the next liquid flow.

BACKGROUND ART

Recent rapid development of the biotechnology expands a demand of a flow cytometer and a cell sorter which are more commonly used in the various fields of medicine and biology for automatic analysis and fractionation of multiple cells.

In general, the flow cytometer forms a stream of a sheath flow containing various cell particles aligned in line, which are collected from a living body (blood, etc.) and dyed with a fluorescent labeling reagent, and emits laser beam onto the stream of the cell particles to detect light excited by and/or scattered at the cell particles (i.e., forward-scattered light, and side-scattered light, and multicolor fluorescence varying based on the fluorescent labeling reagent in use) so that each of the cell particles in the stream is analyzed based upon the detected light.

Also the flow cytometer converts the detected light having identification information unique to each of the cell particles into electrical signals, so as to statistically evaluate electrical signals for a mass of the cells collected from the sample, thereby allowing diagnosis of a pathologic condition such as a disease of the living body.

Further the cell sorter uses the electrical signals having identification information of the cell particles to selectively charge droplets containing a particular group of the cells to be sorted, and forms a DC electrical field between a pair of deflectors across a dropping path of the droplet, thereby selectively retrieving or sorting the desired cells.

Especially recent development has proved great efficacy and possibility of the immune cell therapy and/or the stem cell therapy using own stem cells, for which more intensive research is being made. In such research, it is important to establish the technique for sorting or isolating the desired cell particles from the sample liquid. Practically, when the cell sorter is used for sequentially sorting various types of the cell particles within different liquid flows, one of the cell particles in the first liquid flow may possibly be remained somewhere in a system of the cell sorter and mixed with the second liquid flow which is later processed. Thus, it has been reported that according to the conventional art, the sample cell particles might be carried over in the cell sorter and contaminated with the other liquid flow. Also it has been concerned that when the cell particles to be sorted contain HIV virus or hepatitis virus, those harmful cell particles, which are exposed outside the cell sorter and the sorting chamber or suspended in the air, may cause the biological hazard.

One of prior arts disclosed in U.S. Pat. No. 6,880,414 (of which patent family is Japanese Patent Application Publication 2004-69706) teaches a cell sorter which detects an error when the liquid flow containing HIV virus or hepatitis virus is leaked as droplets or aerosol from the sorting block, and uses collection baskets associated with the fin for aspirating droplets and aerosol to a waste or retrieval container.

However, although the cell sorter disclosed in the aforementioned prior art may aspirate some droplets and aerosol from the sorting block, it can hardly recover droplets and aerosol once attached on the sorting chamber. Also according to the prior art, while the droplets and aerosol containing the infectious viruses attached on the sorting chamber may again be evaporated and suspended in the air, the cell sorter may recover them only during activation of the aspirator, but the infectious viruses may be suspended and diffused after deactivation of the aspirator, which brings risks of the infection to workers including operators of the cell sorter. Thus, according to the prior art, the cell sorter cannot be used for the next sorting operation while the aspirator is being activated to aspirate the droplets and aerosol.

Further the above-mentioned cell sorter fails to even address the problem of the cell particles carried over or remained upstream the sorting chamber such as in a sample-liquid flow mechanism, a flow cell, and a strobe block, which may be contaminated in another liquid flow.

Therefore, the present invention is made for solving such a problem, and one aspect of the present invention is to provide a flow cytometer and a cell sorter eliminating or substantially reducing the possibility that the cell particles within the liquid flow processed in the previous sorting step are remained in components of the system such as a sample-liquid flow mechanism, a flow-defining block, a strobe block, and a sorting chamber, and contaminated in another liquid flow processed in the successive sorting step.

SUMMARY OF INVENTION

One embodiment of the present invention is to provide a system for sorting cell particles in a liquid flow, which comprises a flow-defining block including a flow chamber receiving a sample conduit and a flow cell having a flow channel. The system also comprises a strobe block including a imaging device for taking an image of a jet flow ejected from the flow-defining block and a plurality of droplets in a given image area. The flow-defining block and the strobe block is detachably connected each other.

Also the strobe block includes a nozzle plate having a nozzle channel between a receiving end and a nozzle. The flow-defining block includes a discharge end opposite to the receiving end and a channel enlarged portion of which cross section taken along a predetermined plane perpendicular to a flow direction has an area increasing towards the discharge end. The discharge end and the receiving end have substantially the same open distance L in the predetermined plane perpendicular to the flow direction.

The nozzle plate is detachably connected with the flow-defining block within a predetermined alignment tolerance d, and the open distance L may be ten times or greater than the alignment tolerance d.

Preferably, the open distance L may be 0.3 mm or more.

Furthermore, the sample conduit preferably has a sample tube which is detachably inserted within and extends through the sample conduit along a flow-channel central axis.

The system further includes a block holder detachably connected with the strobe block, for detachably holding the flow-defining block. Also the block holder may include a connection channel between the discharge end of the flow-defining block and the receiving end of the flow channel, and the connection channel has an open distance L substantially the same as those of the discharge end and the receiving end in the predetermined plane perpendicular to the flow direction.

The system further includes an optical source irradiating excitation light onto each of the cell particles running in the liquid flow. The flow-defining block may include a first collective lens having a hemispherical or nonspherical shape opposite to the flow channel, for collimating a fluorescence from each of the cell particles.

In addition the flow-defining block may include a second collective lens for focusing the collimated fluorescence onto an optical fiber, which has a diameter greater than that of the first collective lens.

The system further includes an oscillator detachably connected with the flow-defining block, for applying oscillation to the flow-defining block at a predetermined frequency.

Preferably the oscillator is shaped with a doughnut configuration.

The system further includes a sorting chamber having a pair of deflectors applied with a DC voltage. The sorting chamber may be detachably connected with the flow-defining block and the strobe block.

Also the deflectors may be detachably connected with the sorting chamber.

Furthermore, the sorting chamber may be detached from the strobe block after the deflectors are detached from the sorting chamber.

Furthermore, the strobe block may include a skirt member for hermetically sealing the sorting chamber when the strobe block is assembled with the sorting chamber.

BRIEF DESCRIPTION OF DRAWINGS

FIGS. 3A-3C are enlarged cross sectional views showing lower portions of a sample conduit and a sample tube according to one embodiment of the present invention.

FIGS. 5A, 5B are enlarged cross sectional views showing potions of a flow-defining block and a nozzle plate according to one embodiment of the present invention.

DETAILED DESCRIPTION OF PREFERRED EMBODIMENTS

Referring to attached drawings, embodiments of a system for sorting biological particles contained in a liquid flow such as a cell sorter according to the present invention will be described herein. Although the cell sorter will be exemplarily illustrated herein for facilitating clear understandings of the present invention, it may be applied equally to a flow cytometer as well. In the description, a couple of terms for indicating the directions (for example, "upper" and "lower", etc.) are conveniently used, it should not be interpreted that those terms limit the scope of the present invention.

Figure 1:
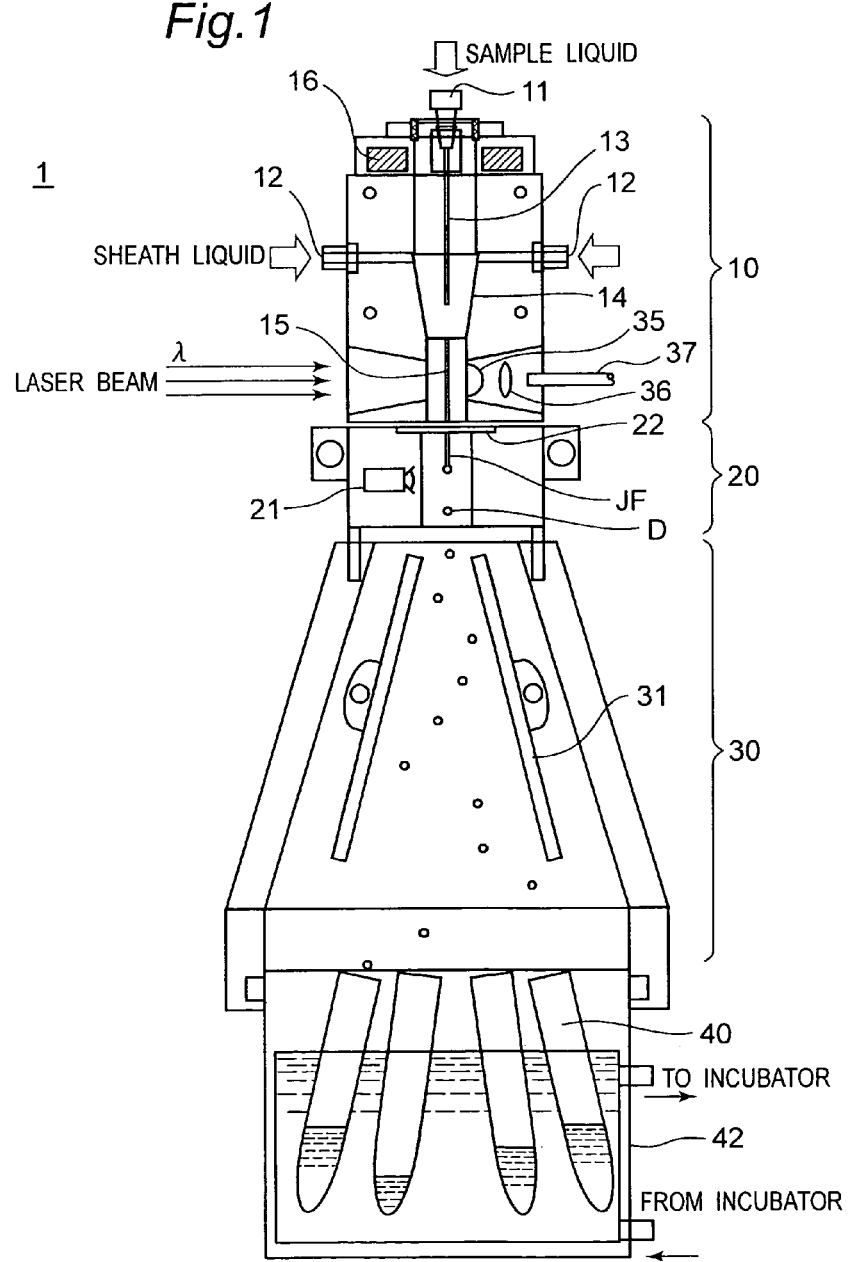
FIG. 1 is a schematic overall view of a cell sorter according to one embodiment of the present invention, showing a general structure thereof.
Figure 2:
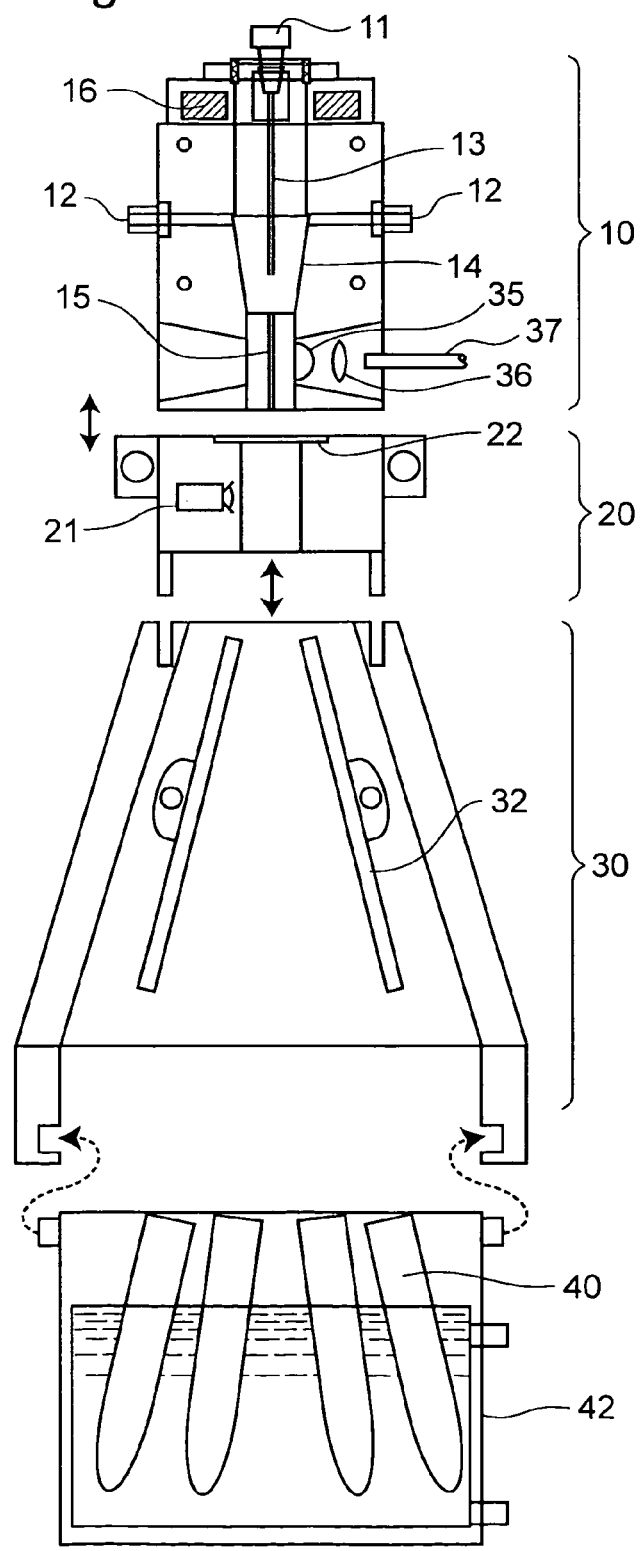
FIG. 2 is an exploded view of the cell sorter according to one embodiment of the present invention, illustrating major components thereof.

FIG. 1 is a schematic overall view of a cell sorter showing a general structure thereof according to one embodiment of the present invention, and FIG. 2 is an exploded view of a cell sorter according to one embodiment of the present invention, illustrating major components thereof. The cell sorter 1 generally comprises a flow-defining block 10, a strobe block 20, a sorting chamber 30, and a collection tube holder 42 holding a plurality of collection tubes 40. Although not illustrated, the cell sorter 1 also comprises a flow supplying mechanism including a sample-liquid supplying system and a sheath-liquid supplying system. The sample-liquid supplying mechanism is adapted to supply the flow-defining block 10 with a sample liquid containing a cell particles P dyed with a fluorescent labeling reagent, and the sheath-liquid supplying system is adapted to supply the flow-defining block 10 with a sheath liquid. It should be noted that each of the above components of the cell sorter 1 of the present invention is detachably assembled, which will be described hereinafter. Several commonly assigned U.S. patents U.S. Pat. Nos. 7,443,491 and 7,417,734, and as well as U.S. Patent Publication Nos. 2009-0122311 and 2010-0297759 are incorporated herein by reference into the present application.

Figure 4B:
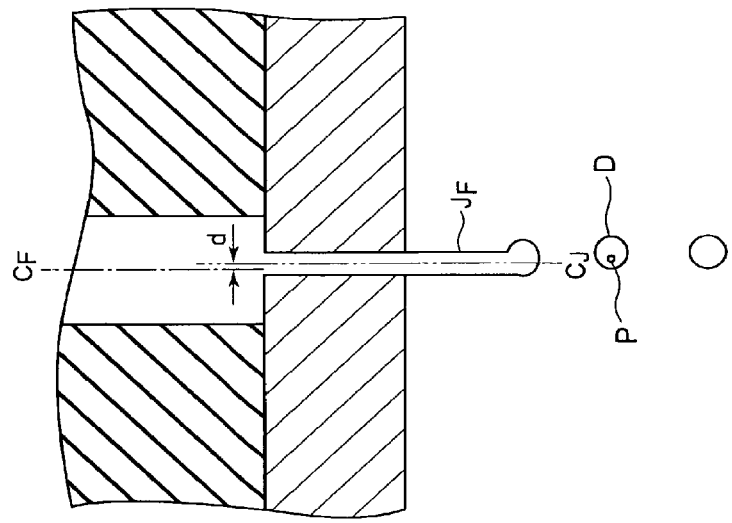
FIGS. 4A, 4B are enlarged cross sectional views showing potions of a flow-defining block and a nozzle plate according to the prior art.

[1. Flow-Defining Block] The flow-defining block 10 includes a sample inlet 11, a sheath inlet 12, and a sample conduit 13 which is made of rigid metal such as stainless and hermetically sealed and inserted within the sample inlet 11. The flow-defining block 10 is designed to guide the sample liquid through the sample conduit 13 and the sheath liquid through the sheath inlet 12 into a flow chamber 14. The flow-defining block 10 is structured to define a stream of cell particles P dyed with a fluorescent labeling reagent, each arranged in line within a flow channel 15 along its central axis $C_F$ (as shown in FIGS. 4B and 5B).

The flow-defining block 10 also includes an oscillator 16 having a piezo-actuator (PZT) oscillating at a given frequency (e.g., f=60 kHz). The oscillator 16 is designed to apply oscillation to the flow-defining block 10 together with a jet flow $J_F$ ejected through a nozzle 24 of a nozzle plate 22 (as described later), thereby splitting the jet flow to a plurality of droplets D at the break-off point. Thus, the frequency of the oscillator 16 is selected such that each of the droplets D contains a single cell particle P dyed with a fluorescent labeling reagent.

The cell sorter 1 further comprises an optical mechanism including one or more optical source and optical detector (not shown). The optical source is designed to emit coherent light such as laser beam λ onto each one of the cell particles P arranged in line within the flow channel 15. The optical detector is adapted to detect scattering light and fluorescence from each of the cell particles P, thereby to find identification information unique to each one of the cell particles P. The optical detector is positioned opposite to the flow channel 15 of the flow-defining block 10. Also the optical detector includes one or more first collective lens 35 having a hemispherical or nonspherical shape for collimating the fluorescence from each of the cell particles P, and a second collective lens 36 for focusing the collimated fluorescence onto an optical fiber 37 or optical fiber bundle. The second collective lens 36 has a diameter greater than that of the first collective lens 35 so as to reduce image aberration.

While the flow-defining block 10 can be replaced and/or reassembled in relative to the optical mechanism as stated above, the flow-defining block 10 may be repositioned with deviation along a horizontal direction on the paper of FIG. 1, causing variation of the horizontal distance between the optical fiber 37 fixed at a given position of the optical mechanism and the flow-defining block 10. However, since the first collective lens 35 collimates the fluorescence from each of the cell particles P, adverse impact due to variation of the horizontal position of the flow-defining block 10 is eliminated. In other words, collimating the fluorescence substantially increases the tolerance of variation of the horizontal position of the flow-defining block 10.

Also when the flow-defining block 10 may be repositioned with deviation along vertical and depth directions on the paper of FIG. 1, the first collective lens 35 can correct the deviation so as to substantially increases the tolerance of variation in relative to the optical mechanism.

Thus, there is no step required for aligning the optical axis when the flow-defining block 10 is reassembled with the optical mechanism. This is also applicable to the conventional cell sorter, of which flow-defining block is not detachably assembled with the optical mechanism at the user side.

It should be noted that since any types of the optical mechanisms known in the art may appropriately be used, no further description for the optical mechanism will be made herein.

Also according to one embodiment of the present invention, the sample liquid is supplied from the sample-liquid supplying system through the flexible sample tube 17 that is hermetically inserted within the sample conduit 13 as shown in FIGS. 3A,. Thus, when it is desired to exchange the sample liquid with another one containing different type of cell particles P, it is sufficient to replace the sample-liquid supplying system and the sample tube 17 with new ones, and the sample conduit 13 is not required to be replaced or cleaned because it is not contaminated. Since the sample conduit 13 is hermetically inserted within the sample inlet 11 and exactly aligned with the central axis $C_F$ of the flow channel 15, when exchanging the sample liquid, only insertion of the sample tube 17 within the sample conduit 13 is required to have the sheath flow defining a stream of the cell particles P dyed with a fluorescent labeling reagent, in line within a flow channel 15 precisely along its central axis $C_F$.

As a result, in comparison with the conventional art in which the sample conduit itself is replaced, the bothersome step for aligning the sample conduit 13 with the central axis $C_F$, can be eliminated so that the sample liquid may be exchanged in a simple and quick manner. Also replacement of the sample tube 17 inserted in the sample conduit 13 securely removes the cell particles P remained in the sample tube 17.

FIGS. 3A-3C are enlarged cross sectional view showing lower portions of the sample conduit 13 and the sample tube 17 of the present embodiment of the invention. As illustrated in FIGS. 3A, 3B, the sample conduit 13 may have a restricted portion 13a at the bottom so as to improve the hermetical sealing between the sample conduit 13 and the sample tube 17 and to facilitate exactly positioning the sample tube 17 along the central axis $C_F$ of the flow channel 15. Also as shown in FIG. 3C, the sample tube 17 may be shaped to have the inner diameter larger as closer to the bottom, so that each of the cell particles P released from the sample conduit 13 has running speed consistent with one another regardless the radial position of each of the cell particles P.

The sample tube 17 may be sized to have the inner diameter between about 250-400 μm and formed of poly-ether-etherketone (PEEK) resin, Teflon®, silicone rubber, and Tygon®, and the sample conduit 13 may be made of substantially rigid material such as glass.

The oscillator 16 may be shaped with a doughnut configuration and detachably connected with the flow-defining block 10, for example by means of lock screws. In the conventional cell sorter, it is difficult to sterilize the flow-defining block 10 with precision devices such as the oscillator 16 which is fixedly secured thereon. However, according to the present embodiment of the invention, since the oscillator 16 is designed to detachably be mounted on the flow-defining block 10, it is easy to sterilize the flow-defining block 10 after removing the oscillator 16.

[2. Strobe Block] The strobe block 20 according to one preferred embodiment of the invention uses a rail-lock drive mechanism (not shown) to be detachably connected with the flow-defining block 10 by vertical movement thereof as indicated with double-headed arrows in FIG. 2.

The strobe block 20 uses a imaging device 21 such as a CCD camera to take an image of the jet flow $J_F$ and droplets F separated therefrom in a stationary image area, and to determine the distance between adjacent droplets D or the like. The strobe block 20 also uses an optical source such as a LED lamp blinking or flickering intermittently (like a stroboscopic lamp) and coincidently with frequency of the oscillator 16 to image the jet flow $J_F$ and droplets F which seems like motionless. A controller (not shown) determines the distance between adjacent droplets D based upon the image taken by the imaging device 21, and calculates a delay time for each of the cell particles P to run from the position of detection to the break-off point. The controller also controls a electrical charger (not shown) to apply to nozzle plate 22, a given voltage of polarity selected based upon the detected identification information of the cell particle P contained in each of the droplets D, at timing just before each of the droplets D is estimated to reach at the break-off point.

Figure 4A:
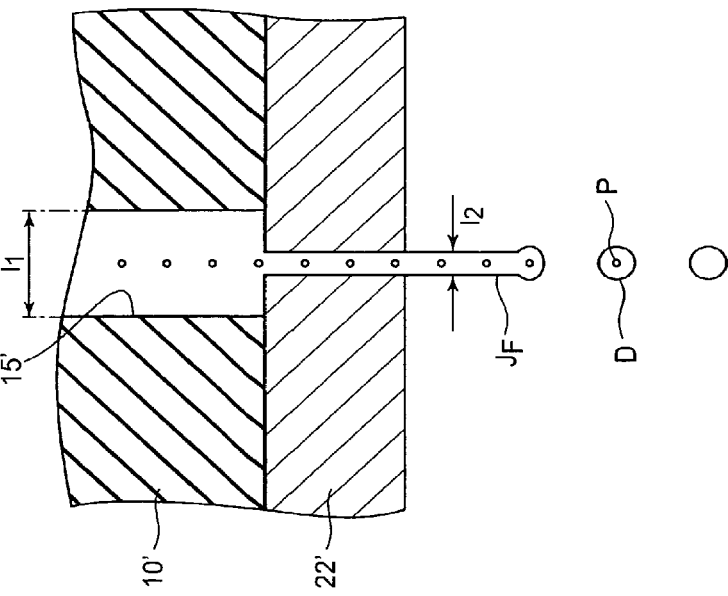

FIGS. 4A, 4B are enlarged cross sectional views showing potions of the flow-defining block 10', the flow channel 15', and the nozzle plate 22' according to the prior art. In FIG. 4A, the flow channel 15' and the jet flow $J_F$ have width (distance) denoted as "$I_1$" and "$I_2$" in a given cross section, respectively. In FIG. 4B, the flow channel 15' and the jet flow $J_F$ also have a flow-channel central axis $C_F$ as indicated by a one-dotted line and a jet-flow central axis $C_J$ as indicated by a two-dotted line, respectively.

Of course, it is ideally desirable to precisely align the nozzle plate 22' (or the strobe block 20') with the flow-defining block 10' through an O-ring or an alignment pin so that the flow-channel central axis $C_F$ is coincident with the jet-flow central axis $C_J$, as illustrated in FIG. 4A, and then to hermetically seal the flow-defining block 10' with the nozzle plate 22'. However, it is practically typical to have a gap d between the flow-channel central axis $C_F$ and the jet-flow central axis $C_J$, within a mechanical alignment tolerance of ±30 μm, for example, as illustrated in FIG. 4B.

Thus, the alignment tolerance d of ±30 μm is inevitable when the nozzle plate 22' (or the strobe block 20') is aligned with the flow channel 15' of the flow-defining block 10' through an O-ring. When the flow-channel central axis $C_F$ is deviated from the jet-flow central axis $C_J$ within the alignment tolerance d, each of the cell particles P runs at a radially-deviated position away from the center of the jet-flow central axis $C_J$. In general, it is well known that a laminar flow has a flow rate which is less at the border (peripheral positions) than at the center, and the cell particle P closer to the border has running speed less than that of the cell particle P running along the jet-flow central axis $C_J$. Therefore, while the frequency of the oscillator 16 is adjusted such that each of the droplets D contains a single cell particle P dyed with a fluorescent labeling reagent, if the running speed of the cell particle P itself is reduced, the cell particle P cannot be contained in the droplet D as estimated based upon the identification information. In other words, when the running speed of the cell particle P is reduced, the desired cell particles P cannot precisely be collected by the cell sorter.

For example, the flow channel 15' has a cross section taken along the vertical or flow direction, which has an area of 150 μm×150 μm (corresponding to a horizontal distance or "width $I_1$" in FIG. 4A) or 250 μm×160 μm, while the jet flow $J_F$ has a cross section taken along the vertical direction, which has an area of 70 μm, 85 μm, 100 μm, or 130 μm (corresponding to a horizontal distance or "width $I_2$" in FIG. 4A). Thus the alignment tolerance d of 30 μm is about 12%-20% of the distance $l_1$, in which even small deviation between the jet-flow central axis $C_J$ and the flow-channel central axis $C_F$ may give considerable impact on variation of the running speed of the cell particles P because of the relatively substantial alignment tolerance d over the width "$l_1$".

FIGS. 5A, 5B are enlarged cross sectional views showing potions of a flow-defining block 10, the flow channel 15, and a nozzle plate 22 according to one embodiment of the present invention. The nozzle plate 22 is designed to be precisely aligned with and inserted in the strobe block 20, and the nozzle plate 22 (or the strobe block 20) is hermetically sealed with the flow-defining block 10 by means of the O-ring 27 or an alignment pin, however as mentioned above, the mechanical alignment tolerance d of ±30 μm is inevitable.

The flow-defining block 10 according to one embodiment includes a flow channel 15 and a discharge end 18 thereof, and the flow channel 15 has a channel enlarged portion 19 of which (horizontal) cross section perpendicular to the vertical direction has an area increasing from the flow channel 15 towards the discharge end 18.

Meanwhile, the nozzle plate 22 has a receiving end 23 and a nozzle channel 25 between the receiving end 23 and the nozzle 24, and at least a portion of the nozzle channel 25 has a (horizontal) cross section perpendicular to the vertical direction, of which area is decreasing from the receiving end 23 towards the nozzle 24. Thus, the nozzle channel 25 according to one embodiment is designed to have a channel reduced portion 26.

Also the discharge end 18 of the flow-defining block 10 and the receiving end 23 of the nozzle 24 are designed to have substantially the same open distance L (e.g., 1 mm) in the horizontal cross section perpendicular to the flow direction.

According to one embodiment of the present invention, since both of the discharge end 18 and the receiving end 23 have the open distance L which is relatively larger than the alignment tolerance d, the deviation between the flow-channel central axis $C_F$ (one-dotted line) and the jet-flow central axis $C_J$ (two-dotted line) gives only negligible impact onto variation of the running speed of the cell particles P because of the relatively small alignment tolerance d over the open distance L. Therefore regardless the alignment tolerance d, the open distance L both of the discharge end 18 and the receiving end 23 allows the cell particles P running along the jet-flow central axis $C_J$ without deviation, thereby to keep the running speed thereof substantially constant. In other words, one embodiment of the present invention relatively reduces variation of the running speed of the cell particles P and the distance between adjacent droplets D due to the inevitable mechanical misalignment of the nozzle plate 22 (or the strobe block 20) with the flow-defining block 10.

More particular, when the open distance L of the discharge end 18 and the receiving end 23 is 1 mm and the alignment tolerance d is ±30 μm, the relative alignment tolerance over the open distance L is about 3.3% which is remarkably improved when comparing with the prior art (12% or more) as discussed above with reference to FIGS. 4A and 4B, which allows the cell particles P arranged along the jet-flow central axis C. Therefore, according to one embodiment of the present invention, when the flow-defining block 10 or the strobe block 20 (or the nozzle plate 22 alone) should be replaced with a new one, or temporarily detached for cleaning the strobe block 20 with fresh running water, regardless the possible misalignment of the tolerance d between the flow-channel central axis $C_F$ and the jet-flow central axis $C_J$, each of the cell particles P can be arranged along the jet-flow central axis $C_J$ to keep the running speed thereof constant and eliminate an adverse effect, thereby to maintain accuracy and precision in analyzing and sorting cell particles P.

Preferably, the open distance L may be designed as being ten times or greater than the alignment tolerance d by which the nozzle plate 22 (the strobe block 20) is aligned with the flow-defining block 10. This corresponds to a relative misalignment of 10% or less over the open distance L, so that the cell sorter 1 can analyze and sort the cell particles P in a more precise manner than the conventional cell sorter. Furthermore, more preferably, the open distance L may be designed as being twenty times or greater than the alignment tolerance d. For example, when the alignment tolerance d is ±30 μm, the open distance L may be 0.6 mm or greater, or the relative misalignment may be 5% or less over the open distance L. More preferably, the open distance L may be 1.2 mm or greater, or the relative misalignment may be 2.5% or less over the open distance L. Although intended to be small, when the alignment tolerance d is inevitably substantial, the open distance L may be designed greater in accordance with the alignment tolerance d.

Also, in FIGS. 5A, 5B, the channel enlarged portion 19 of the flow-defining block 10 and the channel reduced portion 26 of the nozzle plate 22 have cross sections which are illustrated as linearly increasing and decreasing, respectively. However, those are not limited thereto, and the channel enlarged portion 19 and the channel reduced portion 26 may be contoured having a curved surface to be convex upward.

Figure 6:
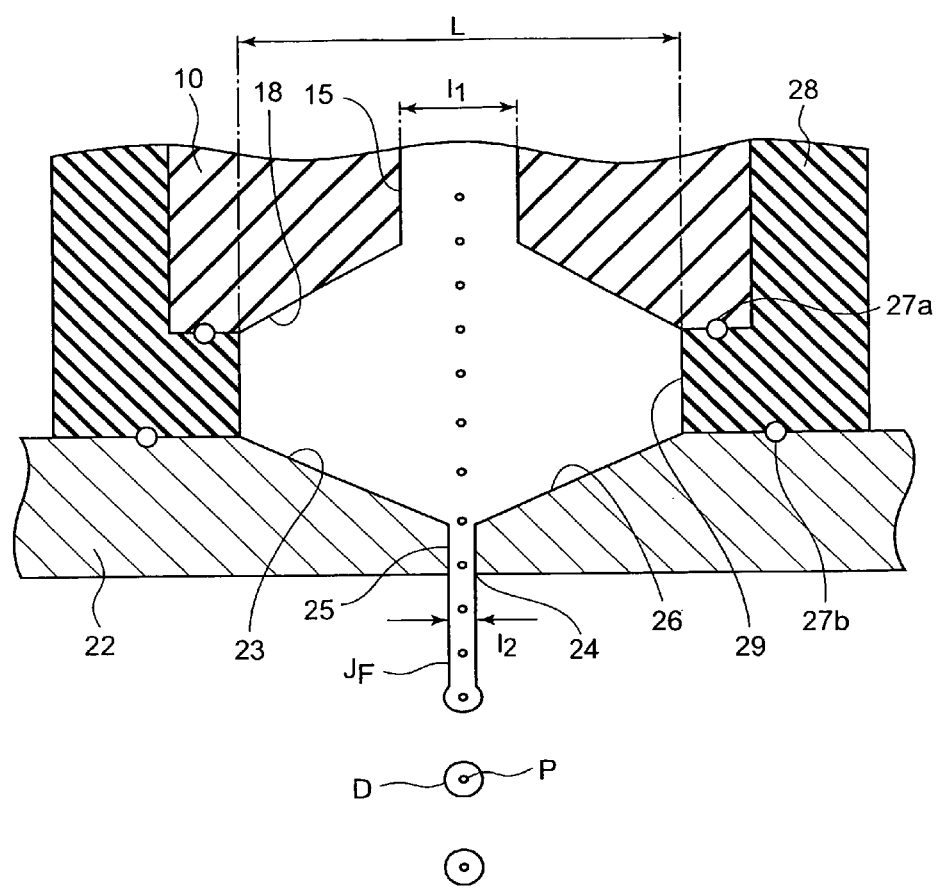
FIG. 6 is an enlarged cross sectional view showing potions of a flow-defining block, a block holder, and a nozzle plate according to another embodiment of the present invention.

Alternatively, according to another embodiment of the present invention, the flow-defining block 10 may have a block holder 28 around the flow-defining block for holding it as shown in FIG. 6. The block holder 28 is sized to have an inner diameter substantially the same as the outer diameter of the flow-defining block 10 so that the flow-defining block 10 is situated and fit within the block holder 28. Also the block holder 28 is detachably and hermetically sealed with the flow-defining block 10 by means of an O-ring 27a and with the nozzle plate 22 by means of another O-ring 27b. The block holder 28 has a connecting channel 29 between the discharge end 18 of the flow channel 15 and the receiving end 23 of the nozzle plate 22, of which cross section is designed to have the open distance L substantially the same as those of the discharge end 18 and the receiving end 23. Therefore, according to the cell sorter so structured, regardless the possible misalignment of the tolerance d between the flow-channel central axis $C_F$ and the jet-flow central axis $C_J$, each of the cell particles P can be arranged along the jet-flow central axis $C_J$ to keep the running speed thereof constant and eliminate an adverse effect, thereby to maintain accuracy and precision in analyzing and sorting cell particles P.

Also when the flow-defining block 10 is formed of fused silica glass, the O-ring 27a between the flow-defining block 10 and the block holder 28 absorbs a shock possibly applied thereto when being detachably assembled, thereby to prevent the flow-defining block from being cracked.

As illustrated by a double headed arrow in FIG. 2, the strobe block 20 can be detachably installed on the sorting chamber 30 by upward and downward movement. The strobe block 20 may include a skirt member covering the sorting chamber 30 and minimizing free space between the strobe block 20 and the sorting chamber 30 (that is, hermetically sealing the sorting chamber 30) once the strobe block 20 is moved downwardly to the sorting chamber 30. The skirt member is adapted to be introduced or guided within the sorting chamber 30 so as to realize an air-tight structure therebetween. Thus the air-tight structure prevents the aerosol possibly containing harmful cell particles P from spreading over the outside of the cell sorter 1, and avoids fluctuation of the air flow, thereby maintaining the jet flow $J_F$ and the droplets D in a stable condition.

For example, the flow-defining block 10 may be replaced with another one for analyzing and sorting various type of cell particles P having different particle diameters, and/or the strobe block 20 (or the nozzle plate 22 alone) may be temporarily detached for cleaning the strobe block 20 with fresh running water. When the strobe block 20 is reassembled with the flow-defining block 10, there may be a misalignment of the tolerance d between the flow-channel central axis $C_F$ and the jet-flow central axis $C_J$. However, as discussed above, regardless the possible misalignment of the tolerance d, thanks to the channel enlarged portion 19 of the flow channel 15 and/or the channel reduced portion 26 of the nozzle channel 25 according to embodiments of the present invention, each of the cell particles P can be arranged along the jet-flow central axis $C_J$ to keep the running speed thereof constant and maintain accuracy and precision in analyzing and sorting cell particles P. Thus, this makes the flow-channel central axis $C_F$ substantially coincident with the jet-flow central axis $C_J$ thereby eliminating the misalignment to the nozzle diameter (corresponding to the width "$I_2$" of 70 μm, 85 μm, 100 μm, 130 μm, etc.). Therefore, even if the nozzle plate 22 is replaced with another one for sorting various cell particles P having different cell diameters, each of the cell particles P can precisely be arranged along the jet-flow central axis $C_J$ without deviation to keep the running speed thereof constant, and maintain accuracy and precision in analyzing and sorting cell particles P.

[3. Sorting Chamber] The sorting chamber 30 includes a pair of deflectors 31 applied with a high voltage (e.g., 7000V) to form the DC electrical field therebetween. On the other hand, the droplet D each containing a single cell particle P is charged through the nozzle plate 22 with a given voltage of a polarity selected in accordance with the identification information unique to the cell particle P. The charged droplet D falling down between the pair of deflectors 31 is effected by the DC electrical field to be deflected towards a certain direction dependent upon the given voltage and the polarity charged thereto.

According to one embodiment of the present invention, the deflectors 31 may also detachably be connected with the sorting chamber 30. Also the sorting chamber 30 itself may be structured to be detachably assembled with the flow-defining block 10 and the strobe block 20 by means of the screw mechanisms and/or alignment pins (not shown) in a precise manner. Preferably, after the deflectors 31 are removed from the sorting chamber 30, and then the sorting chamber 30 is detached from the flow-defining block 10 and the strobe block 20.

Also the sorting chamber 30 may include an air-tight housing having a front door (not shown), in which the deflectors 31 are sterilized with EOG (ethylene oxide gas). Alternatively, only the deflectors 31 are detached from the sorting chamber 30, cleaned with fresh running water, and then reassembled therewith.

In the cell sorter taught in the aforementioned U.S. Pat. No. 6,880,414, it is difficult to recover or aspirate droplets (aerosol and cell particles) attached on the sorting chamber and the deflectors, and therefore, it is impossible to securely prevent the droplets from evaporating again and the harmful cell particles such as the infectious viruses from suspending in the sorting chamber. On the other hand, according to one embodiment of the present invention, since the sorting chamber 30 and the deflectors 31 are designed to be detachably connected in a simple manner, they can surely be kept in an aseptic condition, minimizing evaporation of the harmful cell particles P and risks of the infection for the operators around the cell sorter 1. Also the possibly contaminated sorting chamber 30 and deflectors 31 may be replaced with new ones to initiate next sorting process immediately without awaiting time for completing the cleaning steps of the sorting chamber 30 and deflectors 31.

[4. Collection Tubes and Collection Tube Holder] As illustrated in FIGS. 1 and 2, a collection tube holder 42 for holding a plurality of collection tubes 40 may be detachably connected with the sorting chamber 30. Each of the collection tubes 40 is designed to receive and collect droplets D which are deflected by the deflectors 31 in accordance with the identification information of each of the cell particles in the droplet D. It should be noted that the collection tube holder 42 may received cooling or heating water therein to keep the temperature of the collected droplets D constant as desired, and the cooling or heating water in the collection tube holder 42 may be circulated with an incubator (not shown).

Therefore, since the collection tube holder 42 can easily be detached from the sorting chamber 30, when the sample liquid is exchanged and/or a regular cleaning step is made, the harmful cell particles P causing the risks of infection can securely be removed from the collection tubes 40 and the collection tube holder 42, thereby to keep them in a good aseptic condition.

What is claimed is:

1. A system for sorting cell particles in a liquid flow, comprising:
   a flow-defining block including a flow chamber configured to receive a sample conduit, a flow cell having a flow channel, and a discharge end; and
   a strobe block including an imaging device for taking an image of a jet flow ejected from the flow-defining block and a plurality of droplets in a given image area, and a nozzle plate, which includes a nozzle channel between a receiving end and a nozzle;
   wherein the flow-defining block and the strobe block are detachably connected to each other;
   wherein the discharge end of the flow-defining block is opposite to the receiving end of the nozzle plate;
   wherein the discharge end and the receiving end have substantially the same open distance within an alignment tolerance in a plane perpendicular to a flow direction;
   wherein said strobe block with the nozzle plate inserted therein is detachably connected with the flow-defining block within a horizontal mechanical alignment tolerance inevitably caused in response to connection between said strobe block and said flow-defining block;
   wherein the open distance is ten times or greater than the alignment tolerance; and
   wherein the flow-defining block further includes a channel enlarged portion having a cross section, taken along a plane perpendicular to the flow direction, including an area relatively increasing toward the discharge end; and
   wherein the nozzle plate has a channel reduced portion having a cross section, taken along a plane perpendicular to the flow direction, including an area relatively decreasing from the receiving end toward the nozzle.

2. The system according to claim 1, wherein the open distance is 0.3 mm or more.

3. The system according to claim 1, wherein the sample conduit has a sample tube which is detachably inserted in and extends through the sample conduit along a flow-channel central axis.

4. The system according to claim 1, further comprising a block holder detachably connected with the strobe block, for detachably holding the flow-defining block, wherein the block holder includes a connection channel between the discharge end of the flow-defining block and the receiving end of the plate, the connection channel having an open distance substantially the same as those of the discharge end and the receiving end in the plane perpendicular to the flow direction.

5. The system according to claim 1, further comprising an optical source configured to irradiate excitation light onto each of the cell particles running in the liquid flow; wherein the flow-defining block further includes a first collective lens opposite to the flow channel; wherein the first collective lens is a hemispherical or a nonspherical shape configured to collimate a fluorescence from each of the cell particles.

6. The system according to claim 5, wherein the flow-defining block further includes a second collective lens configured to focus the collimated fluorescence onto an optical fiber and wherein the second collective lens has a diameter greater than the diameter of the first collective lens.

7. The system according to claim 5, further comprising an oscillator detachably connected with the flow-defining block, configured to apply oscillation to the flow-defining block at a predetermined frequency.

8. The system according to claim 7, wherein the oscillator is shaped with a doughnut configuration.

9. The system according to claim 1, further comprising a sorting chamber having a pair of deflectors applied with a DC voltage; wherein the sorting chamber is detachably connected with the flow-defining block and the strobe block.

10. The system according to claim 9, wherein the pair of deflectors are detachably connected with the sorting chamber.

11. The system according to claim 9, wherein the sorting chamber is detached from the strobe block after the deflectors are detached from the sorting chamber.

12. The system according to claim 9, wherein the strobe block further includes a skirt member configured to hermetically seal the sorting chamber when the strobe block is assembled with the sorting chamber.

13. The system according to claim 1, wherein the imaging device is an image capturing housed in the strobe block.

* * * * *